United States Patent [19]
Mader

[11] Patent Number: 6,065,480
[45] Date of Patent: May 23, 2000

[54] DIGITAL PROSTHESIS FOR DENTAL FLOSSING

[76] Inventor: Philip J. Mader, 27 Kenton St., Kensington, Conn. 06037

[21] Appl. No.: 09/293,801

[22] Filed: Apr. 19, 1999

[51] Int. Cl.[7] .................................................. A61C 15/00
[52] U.S. Cl. ......................................... 132/323; 132/325
[58] Field of Search ................... 132/321, 323, 132/325, 326, 324, 327

[56] References Cited

U.S. PATENT DOCUMENTS

| | | |
|---|---|---|
| 3,696,821 | 10/1972 | Adams . |
| 4,050,470 | 9/1977 | Miller . |
| 4,727,895 | 3/1988 | Berarducci ............................. 132/323 |
| 4,926,820 | 5/1990 | Wearn . |
| 5,113,880 | 5/1992 | Narimichi . |
| 5,222,510 | 6/1993 | Zuehlsdorf ............................. 132/323 |
| 5,224,501 | 7/1993 | McKenzie . |
| 5,503,168 | 4/1996 | Wang ..................................... 132/323 |
| 5,678,579 | 10/1997 | Meyer et al. ........................... 132/323 |
| 5,881,745 | 3/1999 | Landis ................................... 132/325 |
| 5,893,379 | 4/1999 | Ghamaty-Azimi ..................... 132/327 |

*Primary Examiner*—Jeffrey A. Smith
*Assistant Examiner*—Pedro Philogene
*Attorney, Agent, or Firm*—David Fink

[57] ABSTRACT

This invention relates to an apparatus for securing and controlling dental floss while in the process of flossing one's teeth. The apparatus comprises a set of prostheses, one for each hand, to reside on a particular digit. Each finger prosthesis has a mechanical attachment point for dental floss. A section of dental floss has each end terminated on the mechanical attachment point. Each finger prosthesis is secured to the user by a mechanical device. The finger prosthesis comprises an adjustable member which extends the floss attachment point beyond the user's finger and or finger nail. The finger prosthesis distributes the mechanical loads encountered during flossing in a comfortable and painless manner over the user's extremities, thus promoting a positive experience and encouraging frequent flossing of one's teeth, all of which leads to better dental and overall health.

16 Claims, 8 Drawing Sheets

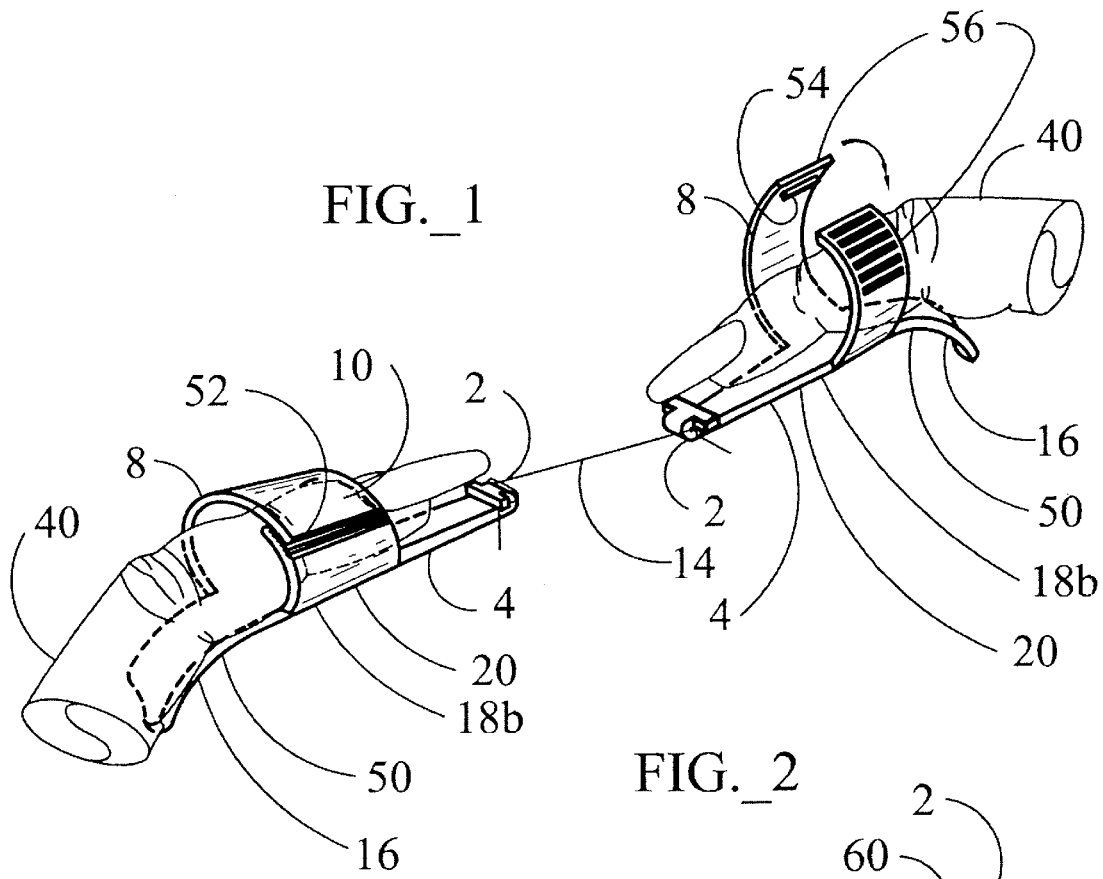
FIG._1
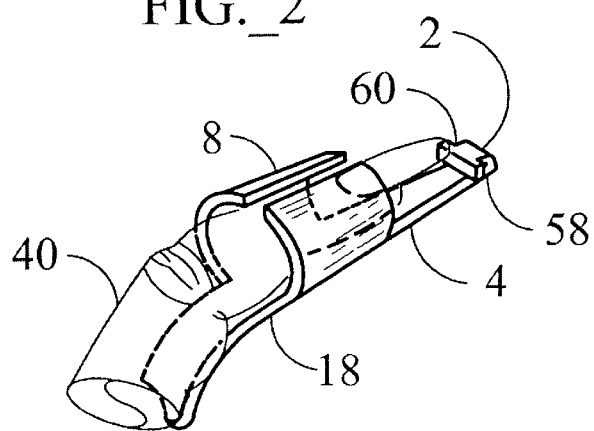
FIG._2

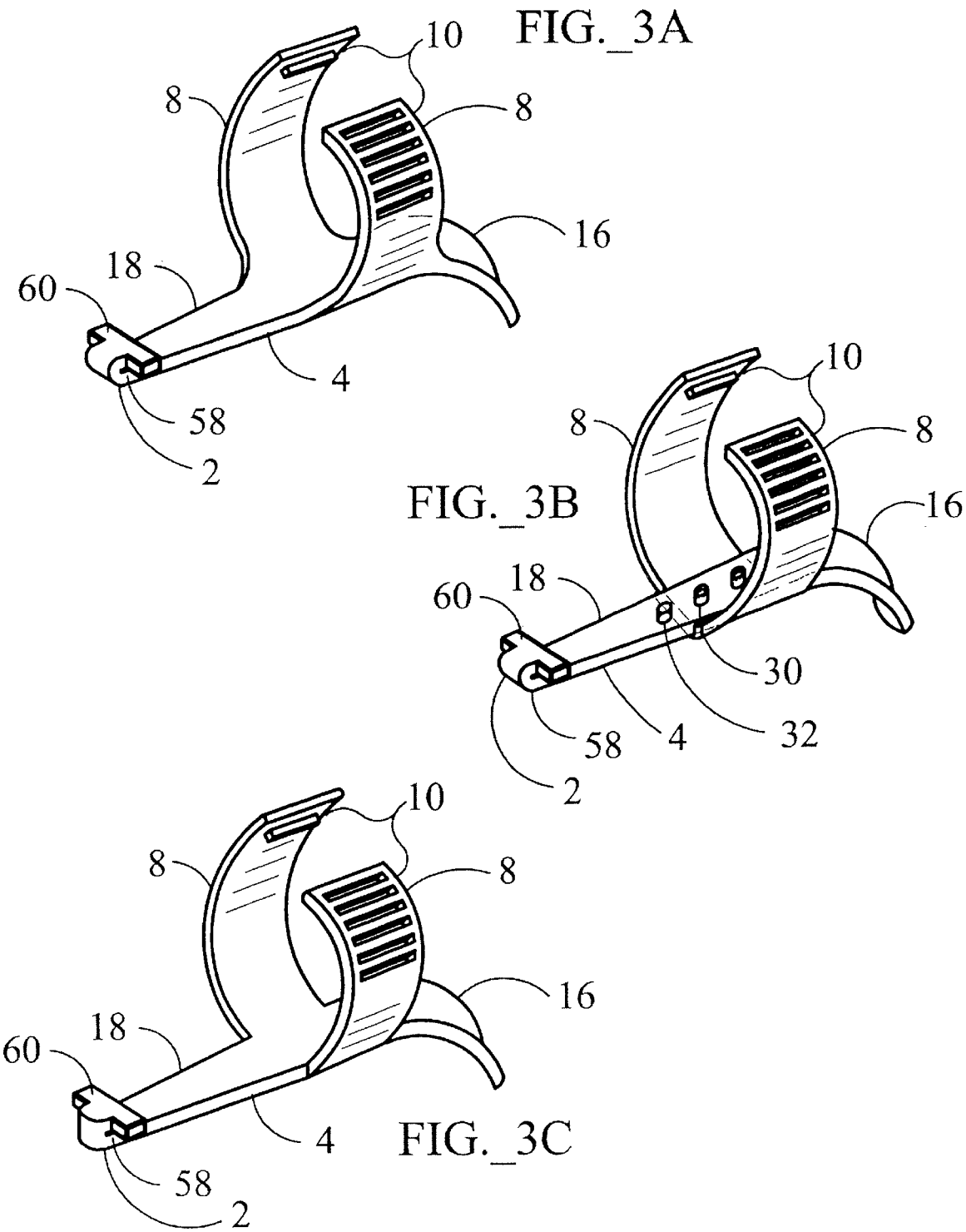

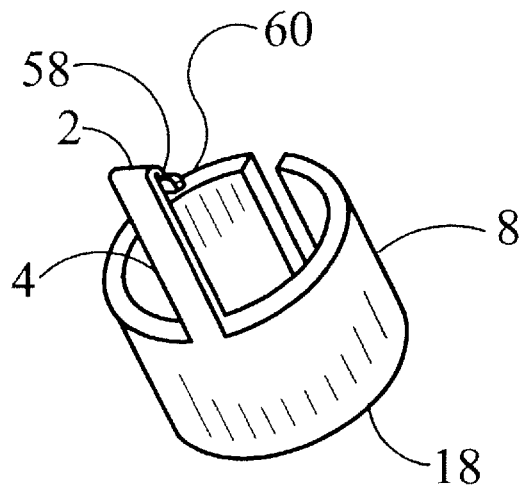
FIG._4A
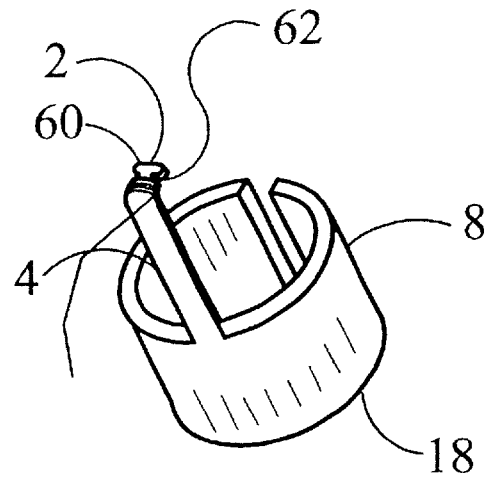
FIG._4B
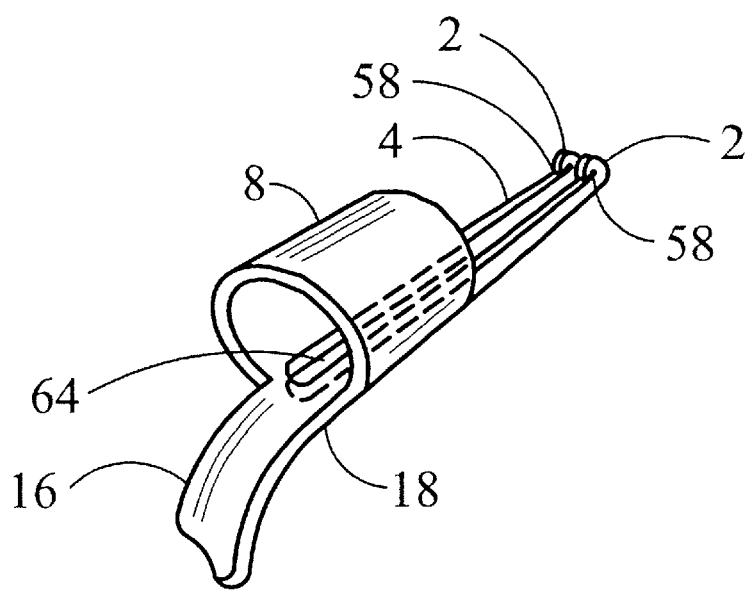
FIG._5

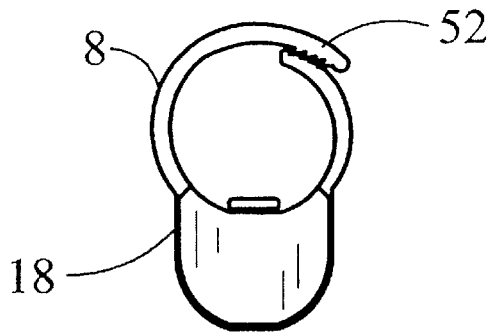
FIG._6
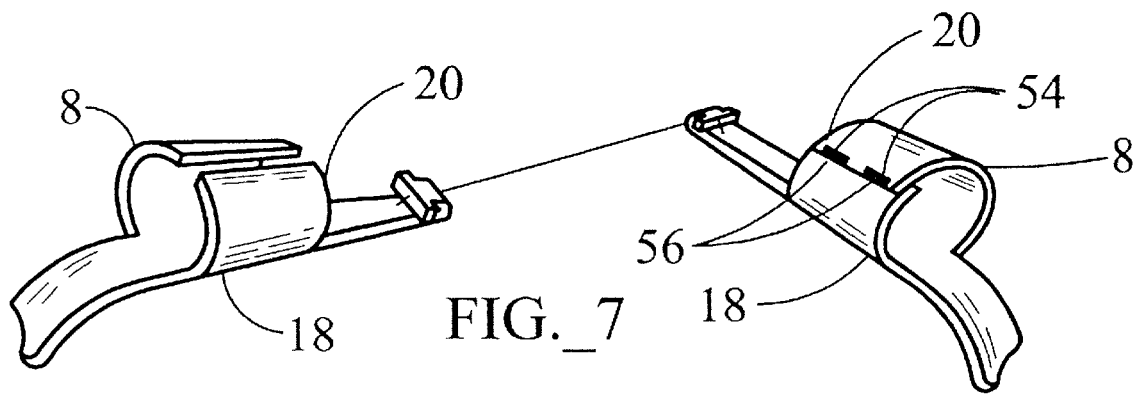
FIG._7
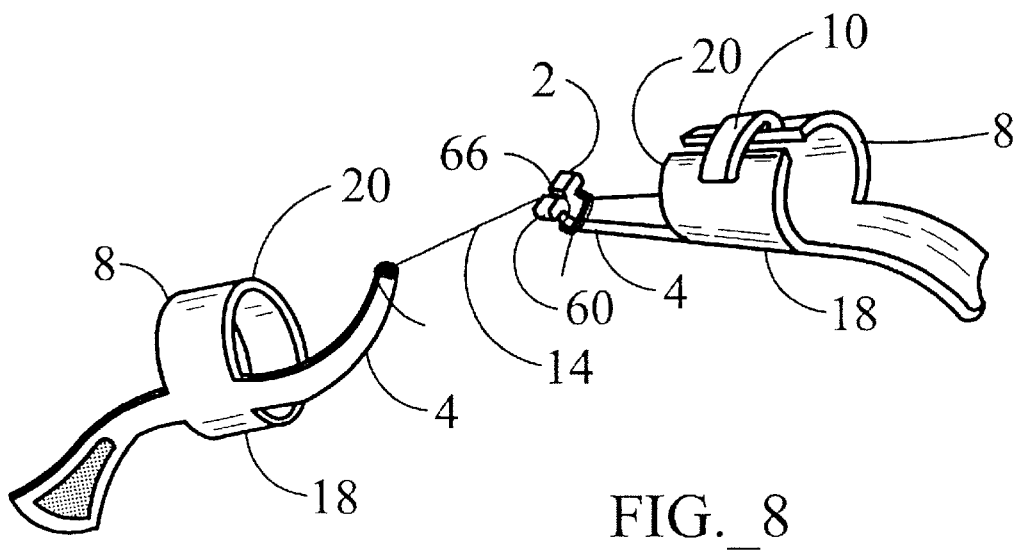
FIG._8

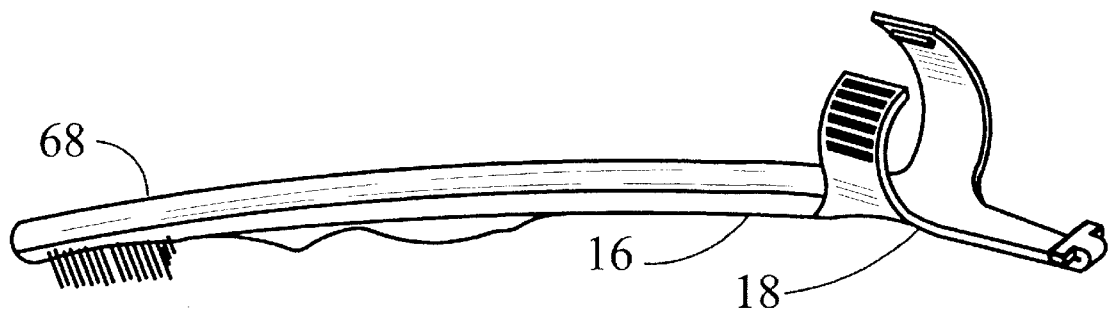
FIG._11A
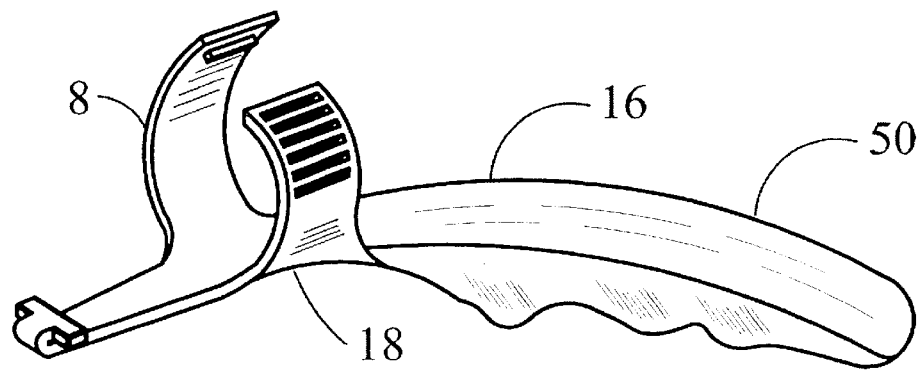
FIG._11B
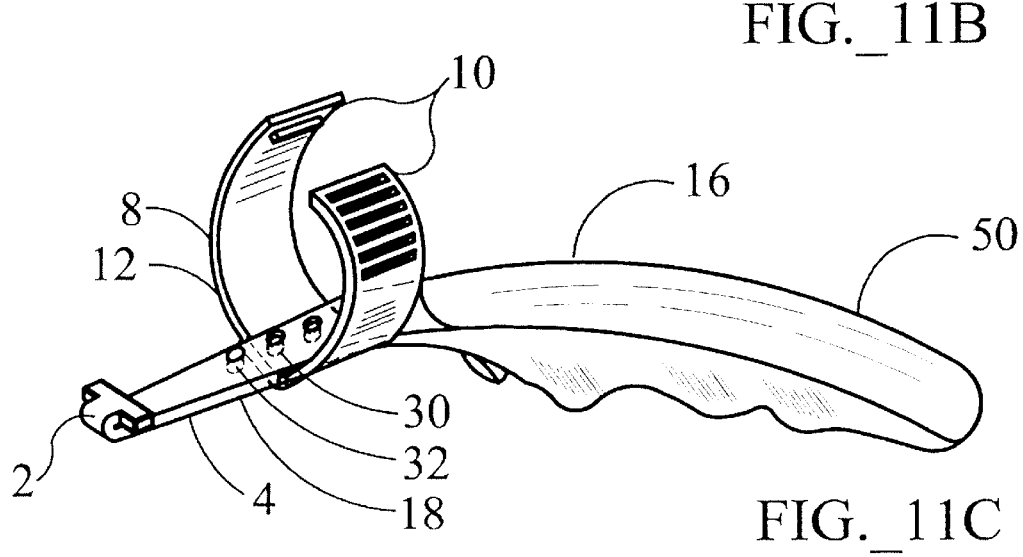
FIG._11C

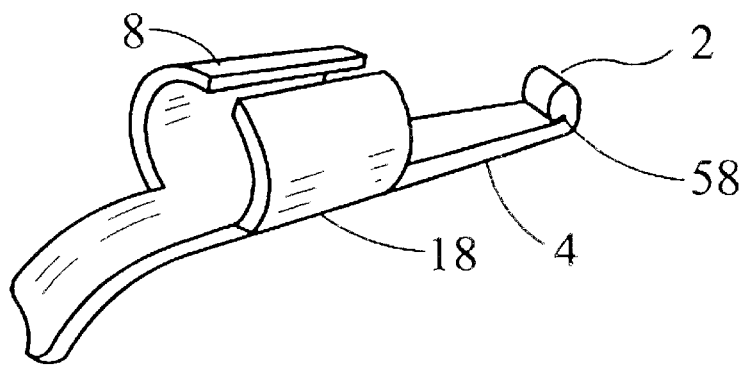
FIG._12A
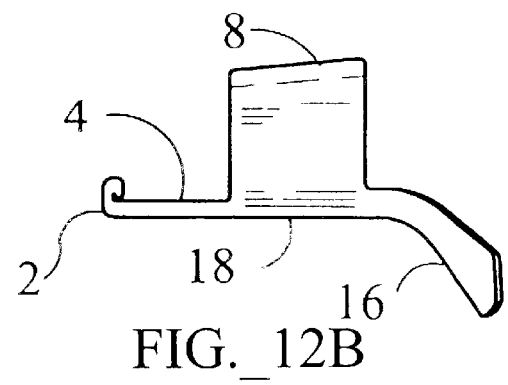
FIG._12B
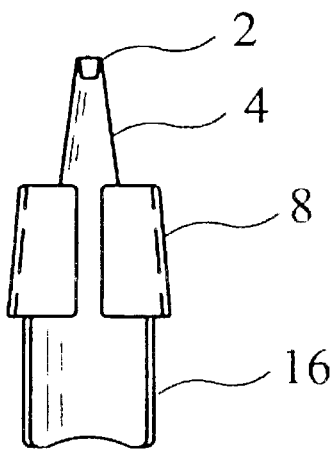
FIG._13A
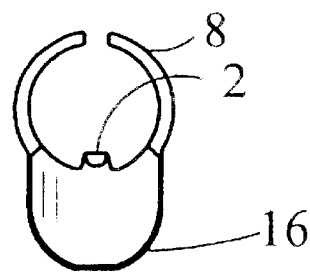
FIG._13B
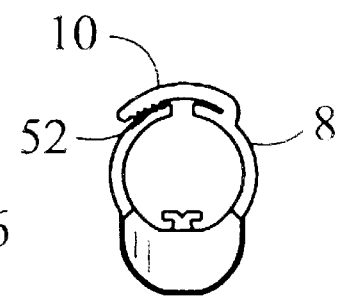
FIG._14

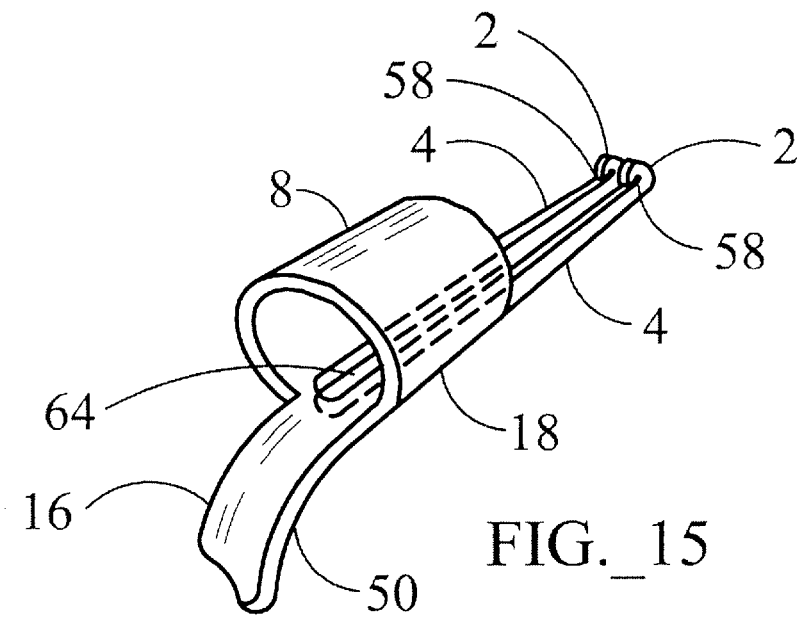
FIG._15
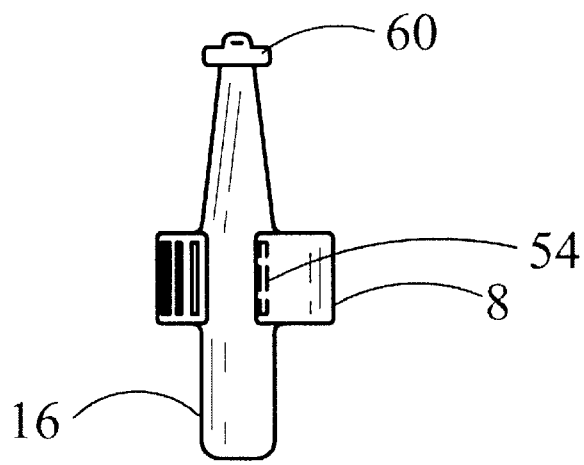
FIG._16A
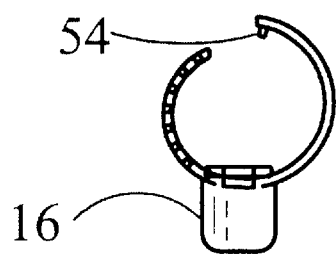
FIG._16B
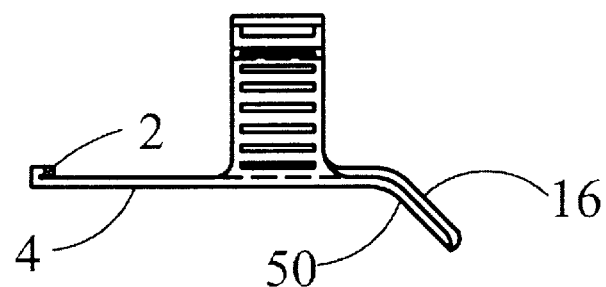
FIG._16C

DIGITAL PROSTHESIS FOR DENTAL FLOSSING

FIELD OF INVENTION

The invention relates generally to devices for flossing, teeth, and more specifically to a finder prosthesis which controls and directs dental floss.

DESCRIPTION OF PRIOR ART

Dental floss is well known and in widespread use to floss the interstitial spaces between teeth. Most people who floss use their fingers and thumbs to control and apply the floss to their teeth. In many cases the floss must be kept taut in order to force it between teeth which are either in physical contact with each other or whose interstitial distance is less than the cross sectional floss diameter. The force required to keep the floss taut and deflect it into tight interstitial areas, especially when adjacent teeth are in surface contact, can be quite high. These forces are transmitted into a very small skin area of the user's digits and often cause pain, decreased circulation, abrasions, and even lacerations. There is a need for a device which can create the necessary floss tension and control yet distribute these forces evenly over a large surface area of the user's digit's, so that the user experiences no pain or discomfort and flossing becomes a more pleasurable experience.

U.S. Pat. No. 3,696,821 to Adams discloses a tooth flossing device. This apparatus comprises essentially a cylindrical rod held in the user's hand. These tools must be gripped by the user and he must use his whole hand to grab each tool or at least two digits of a hand to squeeze and control them. These tools cannot be controlled by a single digit.

U.S. Pat. No. 4,050,470 to Miller discloses a dental floss holder including a pair of separate elongate grip member which hold the dental floss. It is evident that this arrangement does not relieve the user's digits of direct floss contact which can be the cause of pain and discomfort.

U.S. Pat. No. 4,926,820 to Wearn discloses a dental floss assembly comprising a pair of holders but this invention has the same short comings as Miller in that the dental floss comes in direct contact with the user's digits.

Both Miller and Wearn are inherently inefficient in that they only anchor the dental floss in the user's hand. The user still transmits force to the dental floss by using his digits thus experiencing pain and discomfort.

U.S. Pat. No. 5,113,880 to Honda discloses a dental floss and interdental cleaning tool. This apparatus applies a fixed amount of tension to a piece of dental floss and is fixed in its mechanical configuration. This apparatus does not allow for varying the tension of the floss in an efficient manner nor is there any articulation in the apparatus to allow for varying physical approaches to flossing each interstitial space.

U.S. Pat. No. 5,222,510 to Zuehlsdorf discloses a dental ring flosser. This apparatus is worn on a single digit, but it does not extend the floss attachment point beyond the finger tip, nor can the floss tension be varied by the user as he flosses. It also has a very short piece of floss which must be chanced frequently due to its very short length.

U.S. Pat. No. 5,224,501 to McKenzie discloses a tooth flossing, device. This apparatus comprises essentially two elongated tongue depressor shaped tools which are held one in each hand to control and apply a piece of floss attached between the two tools. Because these tools must be gripped by the user, he must use his whole had to grab each tool or at least two digits of each hand to squeeze and control them. These tools cannot be controlled by a single digit.

SUMMARY OF THE INVENTION

The present invention overcomes the disadvantages of the prior art by providing a finger prosthesis which secures one end of the dental floss to a digit and distributes the force load comfortably over a large surface area of the user's finger while directing and controlling the cleansing action of the floss.

It is an object of the invention to provide a finger prosthesis which is adjustable so as to accommodate different size digits, both in length and circumference.

It is another object of the invention to provide a finger prosthesis which is adjustable so as to accommodate different size finger nails, natural or decorative, and protect them from breaking or damage while flossing.

It is a further object of the invention to provide protection to the user's digits from decreased circulation, stress, cuts, abrasions, pain and discomfort.

It is yet a further object of the invention to provide an apparatus for dental flossing which alleviates all the pain and discomfort inherent in manual flossing, creating an experience for the user which promotes frequent flossing thus increasing the dental and overall health of the user.

The invention in a broad embodiment relates to a hand tool apparatus for tensioning and directing a flexible string and or filament, comprising two separate tools, one for each hand, to be worn on a single digit. Each tool has a string attachment means which secures one end of the string to the tool. A clamping means secures the tool to a selected digit. The clamping means and string attachment means are connected by a structural member in a form fitting design whereby the mechanical loads transmitted by the tool are smoothly distributed over the selected digit.

The clamping means may accomplished by a friction fit or adjustable closure with appropriate latching means.

BRIEF DESCRIPTION OF THE DRAWINGS

FIG. 1 is a perspective view of the dental floss apparatus or device embodying the invention with the prosthesis mounted on each finger.

FIG. 2 is a perspective view of a differing embodiment of a dental floss prosthesis or device.

FIG. 3A is a perspective view of a differing embodiment of a dental floss prosthesis or device.

FIG. 3B is a perspective view of a differing embodiment of a dental floss prosthesis or device.

FIG. 3C is a perspective view of a differing embodiment of a dental floss prosthesis or device.

FIG. 4A is a perspective view of a differing embodiment of a dental floss prosthesis or device.

FIG. 4B is a perspective view of differing embodiment of a dental floss prosthesis or device.

FIG. 5 is a perspective view of the entire embodiment of the dental floss prosthesis or device.

FIG. 6 is a rear elevation of the left finger prosthesis in FIG. 1.

FIG. 7 is a perspective view of another embodiment of a dental floss prosthesis or device with different clamp assemblies and floss hooks on each finger prosthesis.

FIG. 8 is a perspective view of another embodiment of a dental floss prosthesis or device with different clamp assemblies, floss hooks on each finger prosthesis and a curved structural member on the left finger prosthesis.

FIG. 11A is a perspective view of another embodiment of a dental floss prosthesis or device as a structural appendage to toothbrush where the finger prosthesis has an adjustable strap clamp and floss hook.

FIG. 11B is a perspective view of another embodiment of a dental floss prosthesis or device where the finger prosthesis has an adjustable strap clamp, extended curved stabilizer, and floss hook.

FIG. 11C is a perspective view of another embodiment of a dental floss prosthesis or device where the adjustable strap clamp assembly may be adjustably attached along the structural member of the finger prosthesis.

FIG. 12A is a perspective view of another embodiment of a dental floss prosthesis or device with a 'C' clamp and rolled floss hook.

FIG. 12B is a side elevation of the finger prosthesis in FIG. 12A.

FIG. 13A is a top plan view of the finger prosthesis in FIG. 12A.

FIG. 13B is a rear elevation of the finger prosthesis in FIG. 12A.

FIG. 14 is a rear elevation of the right prosthesis of FIG. 8 with an adjustable clamp assembly and floss hook on the finger prosthesis.

FIG. 15 is a perspective view of another embodiment of a dental floss prosthesis or device with a tapered clamp assembly and split structural member terminating in two floss hooks on the finger prosthesis.

FIG. 16A is a top plan view of the right finger prosthesis in FIG. 1.

FIG. 16B is a front elevation of the finger prosthesis shown in FIG. 16A

FIG. 16C is a side elevation of the finger prosthesis shown in FIG. 16A.

DETAILED DESCRIPTION OF THE PREFERRED EMBODIMENTS

Figure 9:
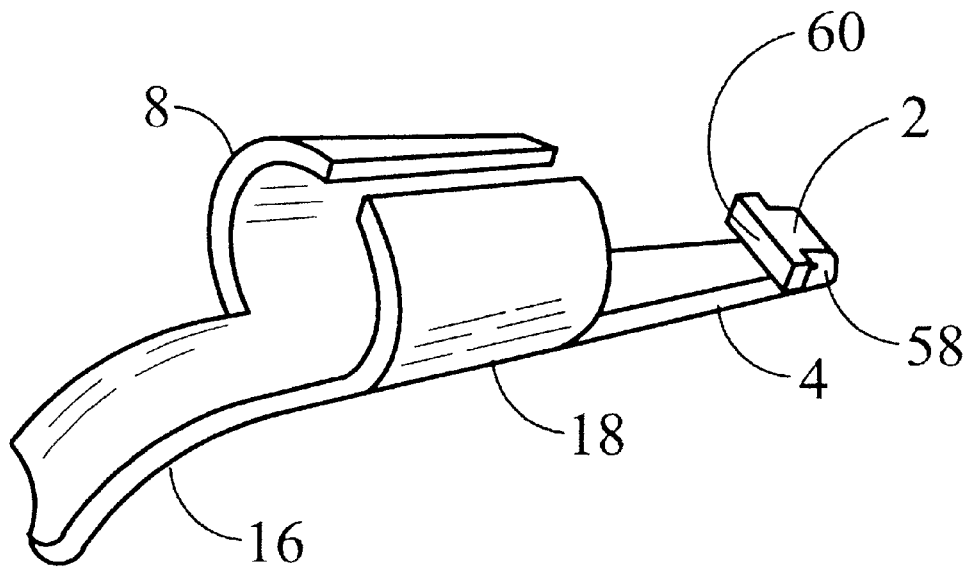
FIG. 9 is a perspective view of another embodiment of a dental floss prosthesis or device with a 'C' clamp and floss hook on the finger prosthesis.

Referring to FIG. 1, an apparatus 20 according to the invention is shown comprising two finger prosthesis 18a, 18b. Dental floss 14 is mechanically secured to a floss hook 2 formed on a structural member 4 which communicates with a finger clamp 8. The floss hook 2 extends beyond the tip of the mounted finger 40 to provide excellent control and to minimize the strain on the finger 40. The clamp 8 is adjustable in size to accommodate users of various dimensions and contains a latch 10 to close the clamp 8. The structural member 4 may extend rearward beyond the clamp 8 to provide a stabilizer 16 which assists the user in controlling and directing the prosthesis 18. The stabilizer 16 extends alone the entire finger 40 and is curved in an arch 50 so as to follow the natural curvature of the user's finger 40. The arch 50 promotes user comfort and control. The stabilizer 16 alone with the clamp 8 and structural member 4 maintain extensive surface contact with the user's finger 40. This area of surface contact between the user's finger 40 and the finger prosthesis 18 is much greater than prior art devices and allows for improved precision and control while distributing the mechanical loads over a greater surface area of the finger 40 thus eliminating damage and pain to the skin of the finger 40. The finger prosthesis 18 may be manufactured in various sizes to accommodate fingers 40 of different length and circumference and is made of a semi-rigid plastic.

The cross sectional dimension of the structural member 4 is sized adequately so as to transmit mechanical forces to the hook 2 without significant deformation of the prosthesis 18. The structural member 4 is dimensioned longitudinally so that the hook 2 extends beyond the user's finger tip or nail 42 when attached to the user's finger 40. This is an important feature because it protects long finger nails from damage while flossing by extending the floss attachment point beyond the user's finger nail 42. The clamp 8 cross sectional dimensions are sized to accommodate flexibility to form around the user's finger 40.

The latch 10 on the left finger prosthesis 18 in FIG. 1 comprises a pair of opposing sawteeth 52 molded into the clamp 8 which can be mated in various positions to adjust the inner circumference of the clamp 8 and thus accommodate different sized fingers 40.

The latch 10 on the right finger prosthesis 18 in FIG. 1 comprises a male rectangular protrusion 54 which is mated to one of several rectangular slots 56 to adjust the inner circumference of the clamp 8 and thus accommodate different sized fingers 40.

A user can control and vary the tension of the floss 14 by varying the mechanical forces applied to the finger prosthesis 18 as a pair. At the same time a user can vary the lateral force applied to the floss 14 which deflects it into the interstitial spaces of teeth. In areas where the adjacent teeth are in surface contact or the interstitial space is smaller than the diameter of the floss 14, this is especially important so that the floss 14 is not accelerated into the user's gums causing pain, damage, and bleeding.

Referring, to FIG. 2, a finger prosthesis 18 is shown with a clamp 8. The user pushes the prosthesis 18 onto her finger until the 'C' type clamp 8 deforms elastically creating a friction fit. The 'C' clamp 8 has a slight taper from one end to the other which is designed to simulate the normal taper of a user's finger 40. The hook 2 is formed in a 'T' shape and then folded back along the structural member 4 to provide an attachment point for the user to wrap the dental floss 14 around. When the 'T' shape is folded back on the structural member 4, a small slit 58 is formed in which the floss 14 is wound into.

Referring to FIG. 3A, a finger prosthesis 18 is shown with a hook 2, slit 58, member 4, clamp 8, latch 10, and stabilizer 16. The entire prosthesis 18 is formed from a mold as a single unit. The hook 2 is formed from a 'T' 60 which is folded back onto the member 4 leaving a small aperture slit 58. The slit 58 is shaped to allow the easy engagement and retention of the dental floss 14.

Referring to FIG. 3B, a finger prosthesis 18 is constructed by combining two assemblies. The clamp 8 and latch 10 are formed into a clamp assembly 12. The hook 2, member 4, and stabilizer 16 are formed into a digit assembly 6. The clamp assembly 19 and digital assembly 6 are snapped together using male posts 30 and female apertures 32. The relative position of the clamp assembly 12 and the digit assembly 6 may be varied so as to adjust the distance between the hook 2 and the camp 8.

Referring to FIG. 3C, a finger prosthesis 18 is shown with a hook 2, slit 58, member 4, clamp 8, latch 10, and stabilizer 16. The entire prosthesis 18 is formed from a mold as a single unit. The hook 2, slit 58, and T 60 are formed together with the prosthesis 18 from a mold.

Referring to FIG. 4A, a finger prosthesis 18 is shown with a hook 2, slit 58, member 4, and clamp 8. The longitudinal dimension of the clamp 8 is increased to provide stability, control, and distribute mechanical loads evenly over the user's finger.

Referring to FIG. 4B, a finger prosthesis 18 is shown with a hook 2, member 4, and clamp 8. The hook is formed by bending the T 60 at a right angle to the member 4. The floss 14 is then wrapped around the waist 62 of the T 60. The longitudinal dimension of the clamp 8 is increased to provide stability, control, and distribute mechanical loads evenly over the user's finger.

Referring to FIG. 5, a finger prosthesis 18 is shown with dual members 4, clamp 8, and stabilizer 16. The clamp 8 is formed as a cylinder of elastomeric material and engages the user's finger in a friction fit. The hooks 2 are formed in this embodiment by folding back the unformed end of each of the dual members 4 leaving a slit 58 for the floss 14 to be wrapped into. The dual members 4 form a 'U' shaped channel 64 extending from the hooks 2 back to the base of clamp 8. The dual members 4 and 'U' channel 64 allow the clamp 8 to deform elasticity and retain the user's finger in the prosthesis 18.

Referring to FIG. 6, a finger prosthesis 18 is shown with a clamp 8 which closes around the user's finger and is firmly secured by sawteeth 52 formed on the clamp 8.

Referring to FIG. 7, an apparatus 20 is shown with two finger prosthesis 18. The left prosthesis 18 has a 'C' type clamp 8, while the right prosthesis 18 has a closing clamp 8 which is secured by protrusions 54 on one side of the clamp 8 which fit into slots 56 on the other side of the clamp 8.

Referring to FIG. 8, an apparatus 20 is shown with two finger prosthesis 18. The left prosthesis 18 has a cylindrical type clamp 8, and curved member 4 which is shaped to accommodate a thumb of a user. The right prosthesis 18 has a 'C' type clamp 8 with a latch 10, and hook 2 comprising a T 60 which is at right angles to the member 4. The T 60 has a notch 66 in the head of the T 60 to keep the floss 14 centered on the hook 2.

Referring to FIG. 9, a finger prosthesis 18 is shown with a hook 2, slit 58, T 60, member 4, tapered 'C' clamp 8, and stabilizer 16. The entire prosthesis 18 is formed from a mold as a single unit. The hook 2 is formed from a 'T' 60 which is folded back onto the member 4 leaving a small aperture slit 58 which engages the floss 14.

Figure 10:
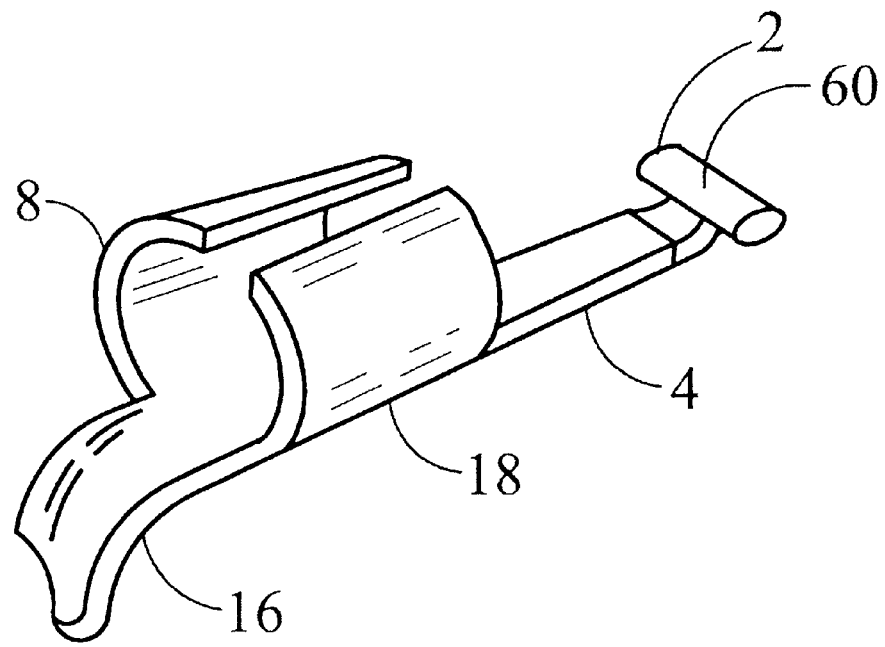
FIG. 10 is a perspective view of another embodiment of a dental floss prosthesis or device with a 'C' clamp and aerodynamic floss hook on the finger prosthesis.

Referring to FIG. 10, a finger prosthesis 18 is shown with a hook 2, T 60, member 4, tapered 'C' clamp 8, and stabilizer 16. The entire prosthesis 18 is formed from a mold as a single unit. The head cross-section of the "T" 60 is aerodynamic in shape and the base of the T 60 is at right angles to the member 4.

Referring to FIG. 11A, a finger prosthesis 18 is shown similar to FIG. 3A except the stabilizer 16 extends straight away from the clamp 8 and forms a toothbrush 68.

Referring to FIG. 11B, a finger prosthesis 18 is shown similar to FIG. 3A except the stabilizer 16 extends further away from the clamp 8 in an arch 50 which will contact the user's palm increasing the amount of control and comfort of the user.

Referring to FIG. 11C, a finger prosthesis 18 is shown similar to FIG. 3B except the stabilizer 16 extends further away from the clamp 8 in an arch 50 which will contact the user's palm increasing the amount of control and comfort of the user. The finger prosthesis 18 is constructed by combining two assemblies. The clamp 8 and latch 10 are formed into a clamp assembly 12. The hook 2, member 4, and extended stabilizer 16 are formed into a digit assembly 6. The clamp assembly 12 and digital assembly 6 are snapped together using male posts 30 and female apertures 32. The relative position of the clamp assembly 12 and the digit assembly 6 may be varied so as to adjust the distance between the hook 2 and the clamp 8.

Referring to FIG. 12A, a finger prosthesis 18 is shown similar to FIG. 2 except the hook 2 is formed by rolling the straight end of member 4 back towards the clamp 8 forming a slit 58 into which the floss 14 maybe secured.

Referring to FIG. 12B, a side elevation of the finger prosthesis 18 in FIG. 12A is shown.

Referring to FIG. 13A, a top plan view of the finger prosthesis 18 in FIG. 12A.

Referring to FIG. 14, a rear elevation of the right finger prosthesis 18 in FIG. 8 is shown with the latch 10 secured by sawteeth 52, the clamp 8 and latch 10 of FIG. 14 form a circular cross section which will grip a finger more comfortably and securely than the clamp 8 and latch 10 of FIG. 6 whose cross section is a spiral, because the cross section of a finger is more a circle than a spiral.

Referring to FIG. 15, a finger prosthesis 18 is shown which is an enlargement of FIG. 5.

Referring to FIG. 16A, a top plan view of the finger prosthesis 18 in FIG. 3C is shown.

Referring to FIG. 16B, a rear elevation of the finger prosthesis 18 in FIG. 3C is shown.

Referring to FIG. 16C, a side elevation of the finger prosthesis 18 in FIG. 3C is shown.

What is claimed is:

1. An apparatus suitable for securing dental floss and directing the floss into the interstitial areas between teeth, comprising a finger prosthesis comprised of an elongated member dimensioned for engaging a side of a finger, said elongated member being flexible to allow the engagement of said finger and to be maintained in position through the springing return of said member; a finger attachment means operable for releasably securing said elongated member to said finger; and floss attachment means on said elongated member positioned to be beyond said finger when said elongated member is attached and shaped to enable the releasable attachment of the dental floss.

2. The apparatus as claimed in claim 1, wherein said elongated member further comprises a curved portion for engaging a portion of said finger comfortably when said finger is partially bent so that said curved portion distributes a mechanical load smoothly over the surface of said finger.

3. The apparatus as claimed in claim 1, wherein the finger attachment means is adjustable to engage fingers of differing diameters.

4. The apparatus as claimed in claim 1, wherein the position of the finger attaching means can be mechanically changed so that the distance between the floss attachment means and the finger attachment means can be changed.

5. The apparatus as claimed in claim 4, wherein the finger attachment means is adjustable to engage fingers of differing diameters.

6. The apparatus as claimed in claim 1, wherein two prostheses are coupled together by said floss so as to allow said two prostheses to operate cooperatively.

7. The apparatus as claimed in claim 4, wherein said elongated member further comprises a curved portion for engaging a portion of said finger comfortably when said finger is partially bent so that said curved portion distributes a mechanical load smoothly over the surfaces of said finger.

8. An apparatus suitable for securing dental floss and directing the floss into the interstitial areas between teeth, comprising at least one finger prosthesis shaped to engage a finger, a finger attachment means operable for securing said prosthesis to said finger; an adjusting means operable for adjusting the location of the engagement of said prosthesis with said finger, wherein the position of the adjusting means on said prosthesis can be mechanically changed so that the distance between the floss attachment means and the finger attachment means can be changed; an elongated member on said prosthesis extending beyond said finger and floss attachment means on the distal end of said member shaped to enable the releasable attachment of the dental floss.

9. The apparatus as claimed in claim 8, wherein the finger attachment means is adjustable to accommodate fingers of differing diameters.

10. The apparatus as claimed in claim 8, wherein two prostheses are coupled together by said floss so as to allow said two prostheses to operate cooperatively.

11. The apparatus as claimed in claim 9, wherein two prostheses are coupled together by said floss so as to allow said two prostheses to operate cooperatively.

12. A system suitable for securing dental floss and directing the floss into the interstitial areas between teeth, comprising a first and second finger prosthesis capable of being coupled together by the dental floss to allow the first and second prosthesis to work together cooperatively, each first and second prosthesis comprising an elongated member for engaging a side of a finger, said elongated member being flexible to allow the engagement of said finger and to be maintained in position through the springing return of said portion; attachment means operable for securing said prosthesis to said finger, said finger attachment means is adjustable to accommodate differing finger sizes; a floss attachment means on the distal end of said elongated member, shaped to enable the releasable attachment of the dental floss and positioned to extend beyond the finger.

13. The system as claimed in claim 12, wherein each of said first and second prosthesis comprises a curved portion for engaging a portion of said finger comfortably when said finger is partially bent so that said curved portion distributes the mechanical load smoothly over a surface of said finger.

14. The system as claimed in claim 12, wherein the position of the adjusting means on each of said first and second prostheses can be mechanically changed so that the distance between the floss attachment means and the finger attachment means can be changed.

15. The system as claimed in claim 13, wherein the position of the adjusting means on each of said first and second prostheses can be mechanically changed so that the distance between the floss attachment means and the finger attachment means can be changed.

16. An apparatus suitable for securing dental floss and directing the floss into the interstitial areas between teeth, comprising at least one finger prosthesis, said finger prosthesis comprising;

a flexible elongated member for engaging the side of a finger;

a first member at a distal end of said elongated member shaped and dimensioned to engage and retain and end portion of dental floss, said elongated member being long enough to extend beyond an engaged finger;

a curved member curving away from said engaged finger when the engaged finger is positioned in a generally straight position, said curved member located on said elongated member distal from said first member; and attachment means for releasably attaching said elongated member to said finger; said attachment means comprising a second member and a third member integrally connected to said elongated member and operable to encircle said finger and to be releasably connected to each other, whereby the apparatus remains attached to said finger.

* * * * *